United States Patent [19]

Wimmer

[11] Patent Number: 5,473,536
[45] Date of Patent: Dec. 5, 1995

[54] METHOD AND SYSTEM FOR CUSTOMIZING THE DISPLAY OF PATIENT PHYSIOLOGICAL PARAMETERS ON A MEDICAL MONITOR

[75] Inventor: Myles S. Wimmer, Redmond, Wash.

[73] Assignee: SpaceLabs Medical, Inc., Redmond, Wash.

[21] Appl. No.: 223,420

[22] Filed: Apr. 4, 1994

[51] Int. Cl.$^6$ .................................................. G06F 159/00
[52] U.S. Cl. ........................................................ 364/400
[58] Field of Search ..................... 364/413.01, 413.02, 364/413.03, 400; 395/156, 157, 159

[56] References Cited

PUBLICATIONS

*User's Guide for the Microsoft Windows Operating System,* Microsoft Corporation, 1992, Chap. 5, Control Panel, pp. 141–147.

SpaceLabs Medical Operations Manual, Patient Care Management System, vol. 1, 1993, pp. Remote Display 1–3, Bed 2–4.

*Primary Examiner*—Donald E. McElheny, Jr.
*Attorney, Agent, or Firm*—Seed and Berry

[57] ABSTRACT

A method and system for customizing the display of patient physiological parameters on a medical monitor are provided. Medical sensors connected to a patient record vital signs for the patient and transmit physiological parameters to the medical monitor. The medical monitor displays selected parameters on a display screen according to instructions from a setup program provided by the present invention. The setup program monitors the output of the medical sensors and presents the user with a real-time view of the parameters mailable for display in a graphical user interface. The graphical user interface allows the user to easily select which parameters will be displayed, how the parameters will be displayed, and where the parameters will be displayed on the display screen.

17 Claims, 7 Drawing Sheets

METHOD AND SYSTEM FOR CUSTOMIZING THE DISPLAY OF PATIENT PHYSIOLOGICAL PARAMETERS ON A MEDICAL MONITOR

TECHNICAL FIELD

The present invention relates generally to a method and system for presenting visual output in a computer implemented display system, and more specifically, to a method and system for customizing the display of a medical monitor.

BACKGROUND OF THE INVENTION

Most modern medical care facilities utilize computer implemented medical monitors to monitor the condition of patients. Medical sensors transmit physiological parameters associated with each patient to a medical monitor which is being watched by medical personnel. A physiological parameter may include both graphical and textual data indicating a life-sign of a patient. For example, a medical sensor such as an electrocardiogram might transmit both an electrocardiograph wave form and an associated pulse rate to a medical monitor. Medical monitors are typically located at each bed-side and at central locations such as nurses stations. The bed-side medical monitors may be stand-alone units or networked units. Networked medical monitors transmit data onto a network so that centrally located medical monitors, as well as other bed-side medical monitors, may display data relating to multiple patients. A bed-side medical monitor's main task is to display physiological parameters that are transmitted from local medical sensors, that is, those medical sensors that are directly connected to the bed-side display monitor. Often times, however, a clinician will want to view a physiological parameter for one patient while attending to another patient. In this case, the clinician must program a bed-side display monitor to display local parameters as well as select remote parameters.

A centrally located medical monitor's main task is to display physiological parameters that are transmitted from medical sensors associated with local beds, that is, those beds that are logically grouped with the centrally located medical monitor. Medical care facilities containing a large number of beds typically divide the beds into logical groups called wards or units, then provide one or more centrally located medical monitors for each unit. Because only a limited number of parameters can be displayed on each centrally located medical monitor at one time, medical personnel have to decide which parameters they would like to monitor and then program the central display monitor accordingly.

Current approaches for programming a medical monitor are non-intuitive. Clinicians, who may be novice computer users, are forced to traverse multiple levels of menus in order to select a particular parameter for display. If the clinician would like to have the selected parameter displayed in a particular area or zone of the display monitor, the clinician must then traverse the menus a second time to select a particular zone. To assign colors, sounds, or other attributes to the display of a selected parameter, the clinician must traverse the menus yet again. Current approaches tend to present the computer network as static by allowing a clinician to select a parameter for display when, in reality, the parameter is no longer available for display. Additionally, some prior approaces offer only a predefined list of parameters that is the same for each bed-side. In reality, a computer network is dynamic—at any time, patients can be checked in and out of the medical care facility, and different types of medical sensors can be connected to or disconnected from the computer system. It is important that monitor programming approaches account for this dynamic information.

SUMMARY OF THE INVENTION

In a preferred embodiment, the present invention provides a method and system for customizing the display of physiological parameters on a medical monitor. Medical sensors connected to a patient record vital signs for the patient and transmit physiological parameters. A medical monitor connected to one or more medical sensors displays selected parameters according to instructions from a setup program provided by the present invention. The setup program monitors the output of the medical sensors and presents the user with a real-time view of the parameters available for display. The setup program also provides the user with an intuitive graphical user interface that allows the user to easily select which parameters will be displayed, how the parameters will be displayed (i.e., what color, tone, volume, etc.), and where the parameters will be displayed (i.e., which display zone of the display screen) on the medical monitor. The graphical user interface also presents the inherent hierachy of networked medical monitors in an easy to understand format.

DETAILED DESCRIPTION OF THE INVENTION

In a preferred embodiment, the present invention provides a method and system for customizing the display of patient physiological parameters on a medical monitor. Medical sensors connected to a patient record vital signs for the patient and transmit physiological parameters. A medical monitor connected to the medical sensors, either physically or by telemetry, displays selected parameters according to instructions from a setup program provided by the present invention. The setup program monitors the output of medical sensors and presents the user with a real-time view of the parameters available for display. The setup program also provides the user with a graphical user interface that allows the user to easily select which parameters will be displayed, how the parameters will be displayed (i.e., what color, sound, etc.), and where the parameters will be displayed (i.e., what area of the display screen) on the medical monitor.

Figure 1:
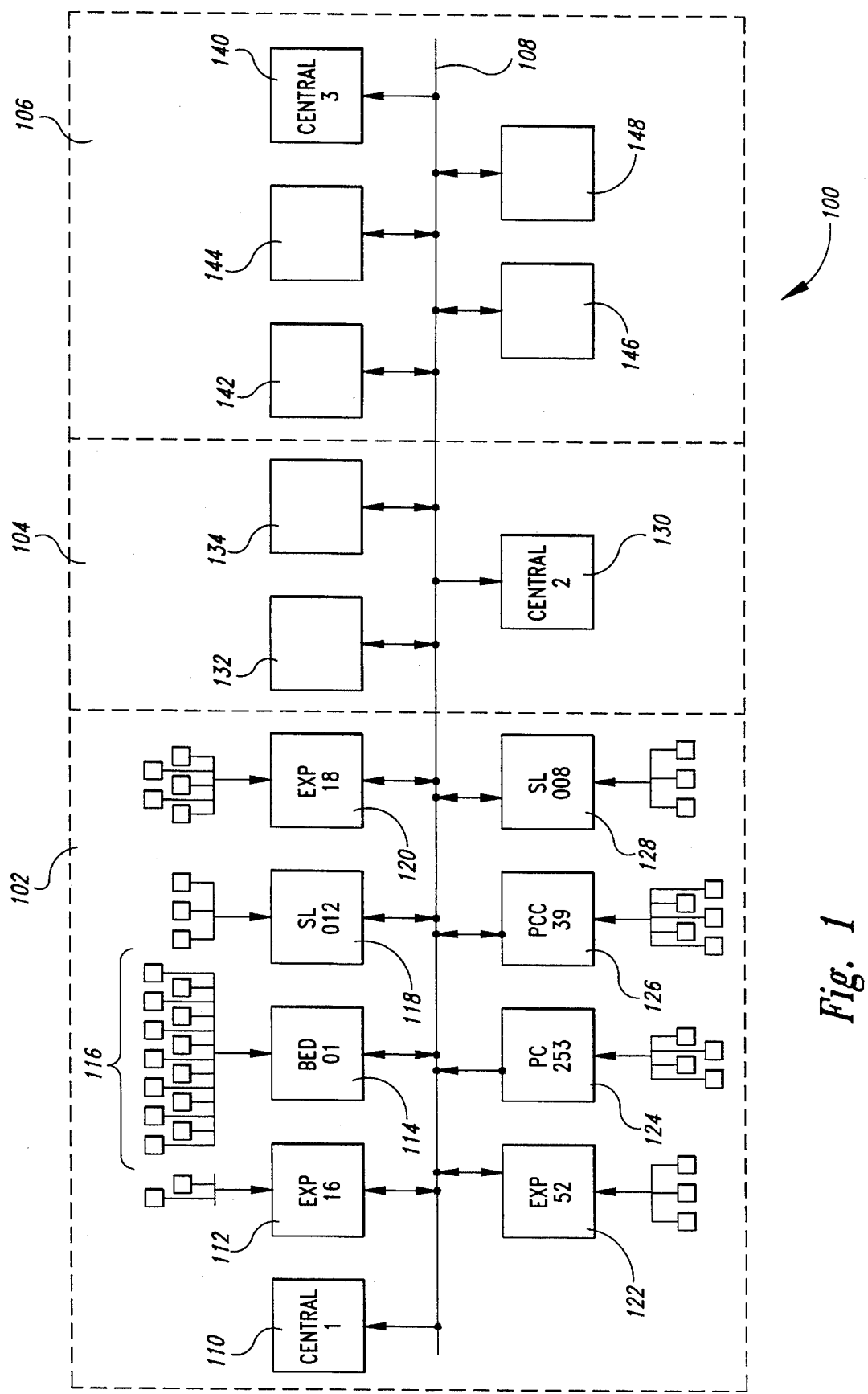
FIG. 1 is a block diagram of an illustrative patient monitoring network.

FIG. 1 is a block diagram of an illustrative patient monitoring network 100. The network 100 is logically divided into three units 102, 104, and 106. Each unit is a logical grouping of bed-side and central monitors. Unit 102 includes bed-side monitors 112, 114, 118, 120, 122, 124, 126, 128 and a central monitor 110; unit 104 includes bed-side monitors 132, 134, and a central monitor 130; and unit 106 include bed-side monitor 142, 144, 146, 148, and a central monitor 140. Each bed-side monitor is connected to one or more modules via a separate network. Each module is connected to one or more medical sensors to provide signals indicative of patient physiological parameters. For example, an ECG module provides signals indicative of a patient's electrocardiogram, and a pulse oximeter module provides signals indicative of the percent of oxygen saturation in vascularized tissues. As shown in FIG. 1, the bed-side monitor 114 is connected to a group of modules 116. Thus, each module in the group of modules 116 receives raw data from one or more medical sensors, converts the raw data to graphical or textual parameters, and then transmits the parameters to the bed-side monitor 114. The bed-side monitor 114 may display all or selected ones of the parameters, and/or transmit the parameters to other monitors, both bed-side and central. The central monitors 110, 130, 140 allow a user to monitor physiological parameters for several patients from a remote location.

Figure 2:
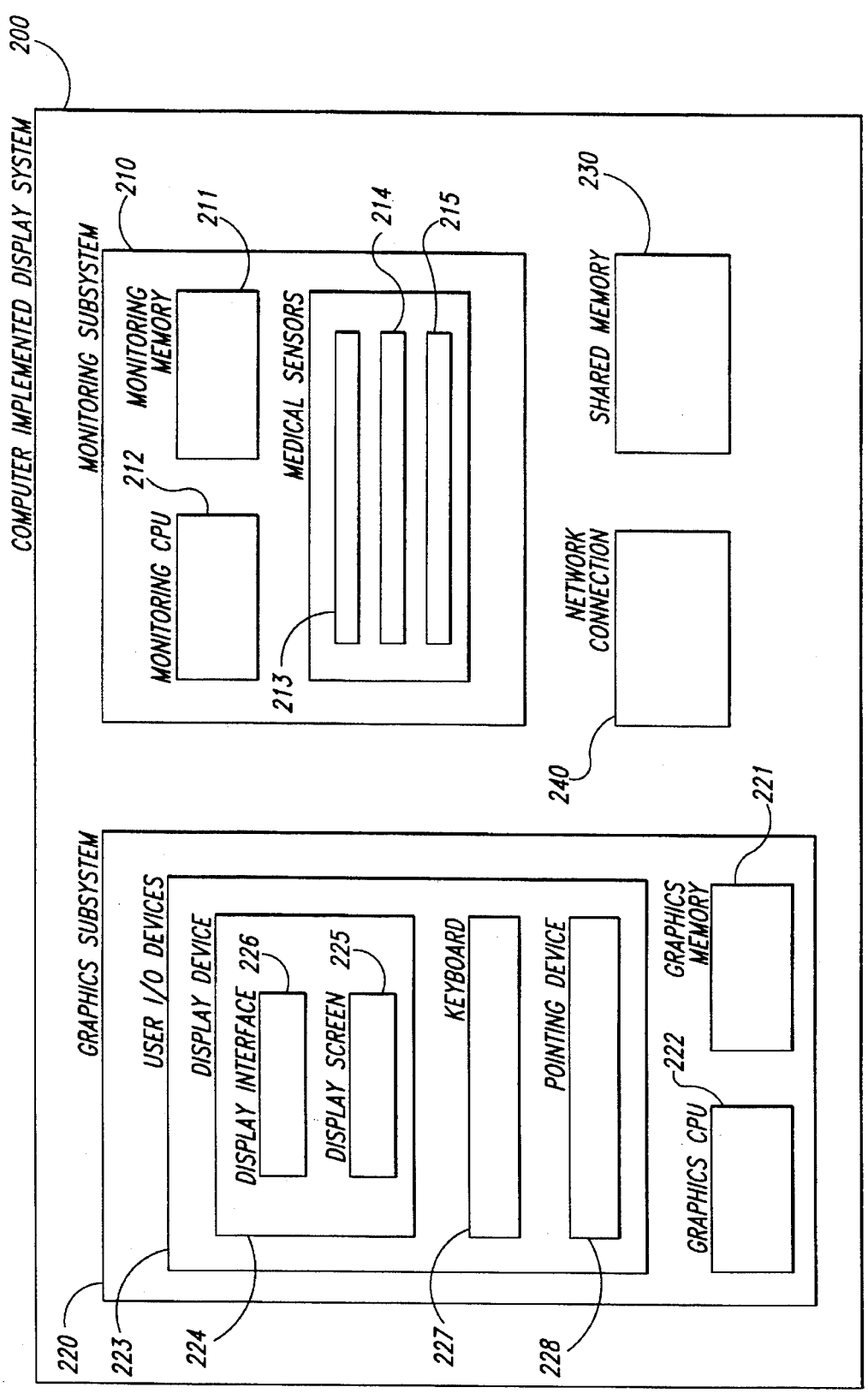
FIG. 2 is a high-level block diagram of a medical monitor including a display screen in accordance with a preferred embodiment of the present invention.

FIG. 2 is a high-level block diagram of a medical monitor 200 in accordance with a preferred embodiment of the present invention. The monitor 200 includes a patient monitoring subsystem 210 for collecting and analyzing patient data, and a graphics subsystem 220 for displaying output and receiving user input. The display system 200 also includes shared memory 230 that may be accessed by both the patient monitoring subsystem 210 and the graphics subsystem 220. The display system 200 further includes a network connection 240 that may be used by both the patient monitoring subsystem 210 and the graphics subsystem 220 to communicate with other monitors.

The monitoring subsystem 210 includes dedicated monitoring memory 211, a monitoring central processing unit (CPU) 212 and medical sensors 213, 214, 215. Examples of medical sensors include electrocardiogram electrodes or pulse oximetry sensors. Data from the medical sensors 213, 214, 215 is stored in the monitoring memory 211 and analyzed by the monitoring CPU 212. The monitoring CPU 212 requests display services from the graphics subsystem 220 in order to display the results of patient data analysis.

The graphics subsystem 220 supports user input/output devices 223 for accepting input from users and displaying information to users. The user input/output devices 223 include a display device 224 comprising a display screen 225 for displaying information, and a display interface 226 for controlling and transmitting information to the display screen 225. The user input/output devices 223 further include a keyboard 227 and a pointing device 228, such as a mouse. The graphics memory 221 is preferably a solid-state memory device whose contents may be permanent or may be loaded from a local disk drive or a remote disk drive controlled by a separate display system to which the monitor 200 is connected via the network connection 240. The above programs execute on a graphics central processing unit 222, or on the central processing unit of a separate display system to which the monitor 200 is connected via the network connection 240.

Figure 3:
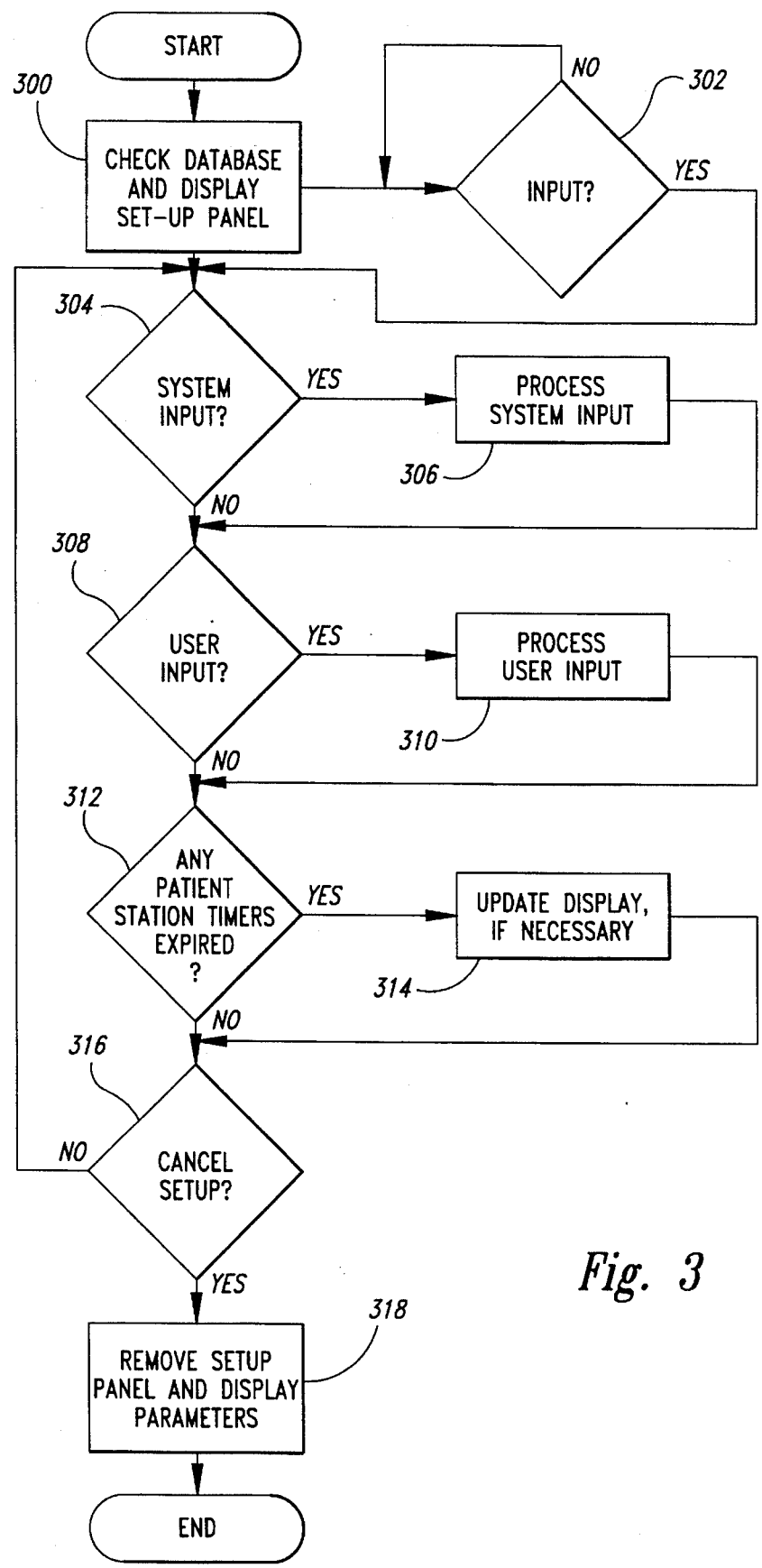
FIG. 3 is an overview flow diagram of a method for customizing the display of patient physiological parameters on the display screen of the medical monitor of FIG. 2 in accordance with a preferred embodiment of the present invention.

FIG. 3 is an overview flow diagram of a method for customizing the display of patient physiological parameters on the display screen 225 of the medical monitor 200 of FIG. 2 in accordance with a preferred embodiment of the present invention. In step 300, the setup program determines the current status of the monitoring network and displays an appropriate graphical user interface on the display screen 225. The current status of the monitoring network includes information such as how many units exist in the network, how many bed-side monitors are associated with each unit, how many parameters are being transmitted by each bed-side monitor, and other status information. This information is typically stored in some type of database that is accessible to the setup program.

Figure 4:
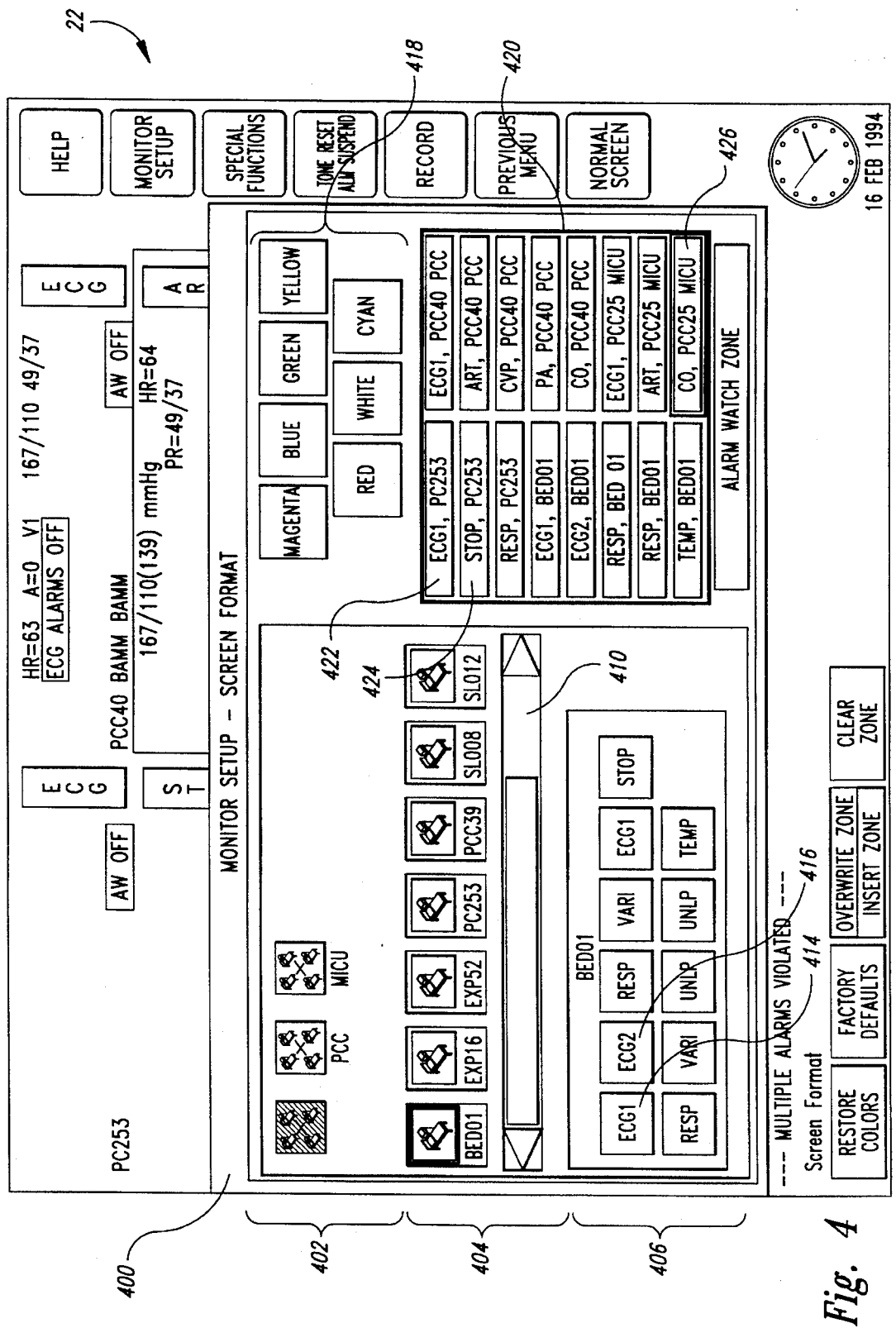
FIG. 4 is a screen print of a graphical user interface used in a preferred embodiment of the present invention to customize the display of patient physiological parameters on the medical monitor of FIG. 2.

FIG. 4 is a screen print of an illustrative graphical user interface 400 displayed on the display screen 225 in a preferred embodiment of the present invention. The information conveyed by the graphical user interface 400 corresponds to the current status of the monitoring network 100 of FIG. 1. The graphical user interface 400 includes a unit area 402, a bed area 404, a parameter area 406, a color area 418, and a zone area 420. The unit area 402 includes one unit indicator for each unit of the monitoring network 100. For example, unit indicator 408 corresponds to unit 102 of the monitoring network 100. The bed area 404 includes one bed indicator for each bed-side monitor in a selected unit. A user selects a unit by activating the unit indicator corresponding to the unit. For purposes of this example, unit indicator 408 is activated. The bed area 404 therefore includes a bed indicator for each bed-side monitor in unit 102. For example, bed indicator 412 corresponds to the bed-side monitor 114. A scroll bar 410 is provided to display additional bed indicators.

The parameter area 406 includes one parameter indicator for each parameter transmitted by a selected bed-side monitor. A user selects a bed-side monitor by activating the bed indicator corresponding to the bed-side monitor. For purposes of this example, bed indicator 412 is activated. The parameter area 406 therefore includes a parameter indicator for each module in the group of modules 116.

The color area 418 includes one color indicator for each color that is available for displaying data on the display screen 225. A user selects a color by activating the color indicator corresponding to the color. The color indicators allow a user to cause a parameter to be displayed on the display screen 225 in a selected color. If no color is selected, a parameter is displayed in a default color, such as white.

Figure 5:
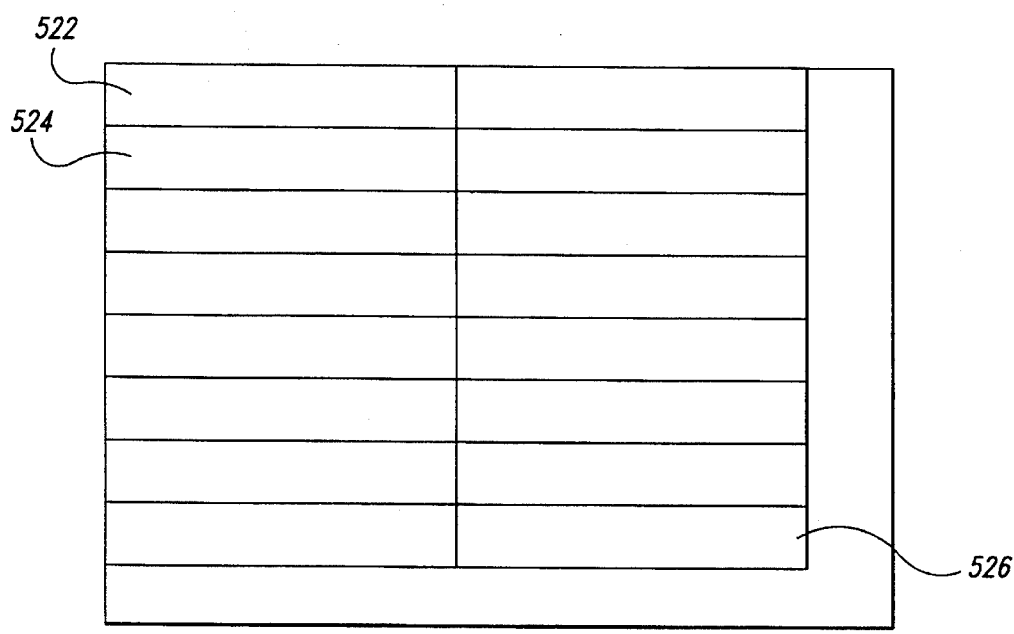
FIG. 5 is a screen print of the display screen of FIG. 2 divided into display zones.

Each parameter is displayed within a display zone of the display screen 225. While the display screen 225 may be logically divided into any arbitrary number of display zones, for purposes of this example the display screen 225 is divided into sixteen display zones. FIG. 5 is a screen print of the display screen 225 divided into display zones. The zone area 420 of FIG. 4 includes one zone indicator for each display zone of the display screen 225 of FIG. 5. For example zone indicator 422 corresponds to display zone 522, zone indicator 424 corresponds to display zone 524, and zone indicator 426 corresponds to display zone 526. When a user selects a parameter and a color and assigns them to a display zone, the selected parameter is displayed in the selected color within the display zone. Indicators for attributes besides color, for example, brightness, alarm tone, alarm destination, and alarm volume, may be also be added to the graphical user interface 400.

Returning to the flow diagram of FIG. 3, in step 302 the setup program determines whether any input has occurred. For purposes of the present invention, the setup program is concerned with two types of input—system input from the monitoring network 100 (FIG. 1) and user input from the graphical user interface 400 (FIG. 4). If no input has occurred, the setup program repeats step 302 until input occurs. When the setup program determines that input has occurred, in step 304 the setup program determines whether the input was from the monitoring network 100, i.e., system input. If system input has occurred, then in step 306 the setup program processes the system input.

Figure 6:
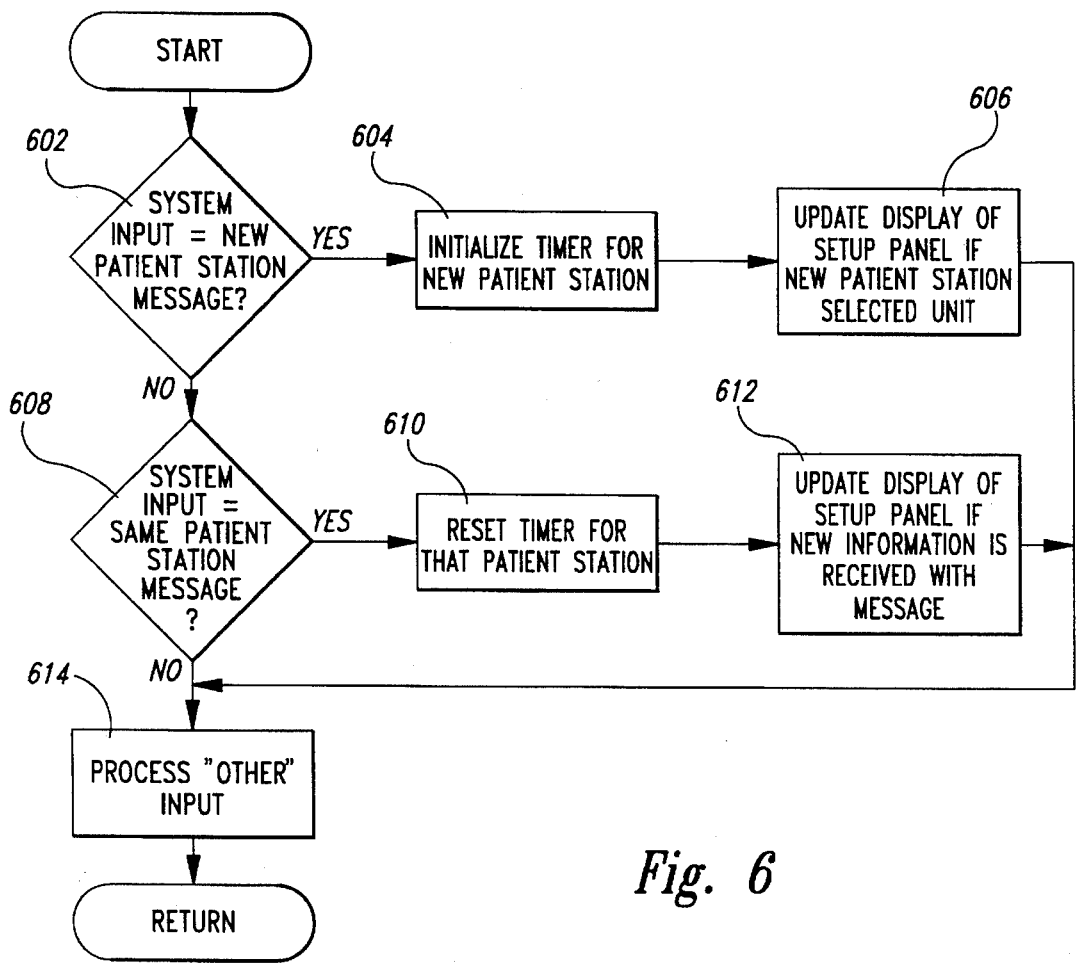
FIG. 6 is a flow diagram of a method for processing system input in accordance with a preferred embodiment of the present invention.

FIG. 6 is a flow diagram of a method used by the setup program to process system input in accordance with a preferred embodiment of the present invention. In step 602, the setup program determines whether the system input is a "new bed" message. A "new bed" message indicates that a new bedside monitor was connected to the monitoring network 100. Each "new bed" message includes information such as which unit is associated with the new bedside monitor and which modules are connected to the new bed-side monitor. If the system input is a "new bed" message, then in step 604 the setup program initializes a timer for the new bed-side side monitor. A timer is used by the setup program to determine when a bed indicator should be removed from the bed area 404. A bed indicator is removed when the bed-side monitor corresponding to the bed indicator is no longer transmitting physiological parameters. In a preferred embodiment of the present invention, a bed indicator is removed from the graphical user interface when a message has not been received from a bed-side monitor for some finite interval of time, for example 30 seconds. A time interval such as 30-seconds allows for common network delays and other minor interruptions. In step 606, the setup program updates the display of the graphical user interface if the new bed-side monitor is associated with the currently activated unit indicator.

If the setup program determines that the system input is not a "new bed" message, then in step 608 the setup program determines whether the system input is a "same bed" message. A "same bed" message indicates that an existing bed-side monitor is still transmitting parameters via the network, but some of the information included within the message may be different than in the last transmission. If the setup program determines that the system input is a "same bed" message, then in step 610 the setup program resets the timer for that bedside monitor. In step 612 the setup program updates the display of the graphical user interface if different information is received within the "same bed" message. Examples of different information include a new patient for an existing bed-side monitor or new information for an existing patient. If the setup program determines in step 608 that the system input is not a "same bed" message, then in step 614 the setup program processes this other input if possible.

Figure 7A:
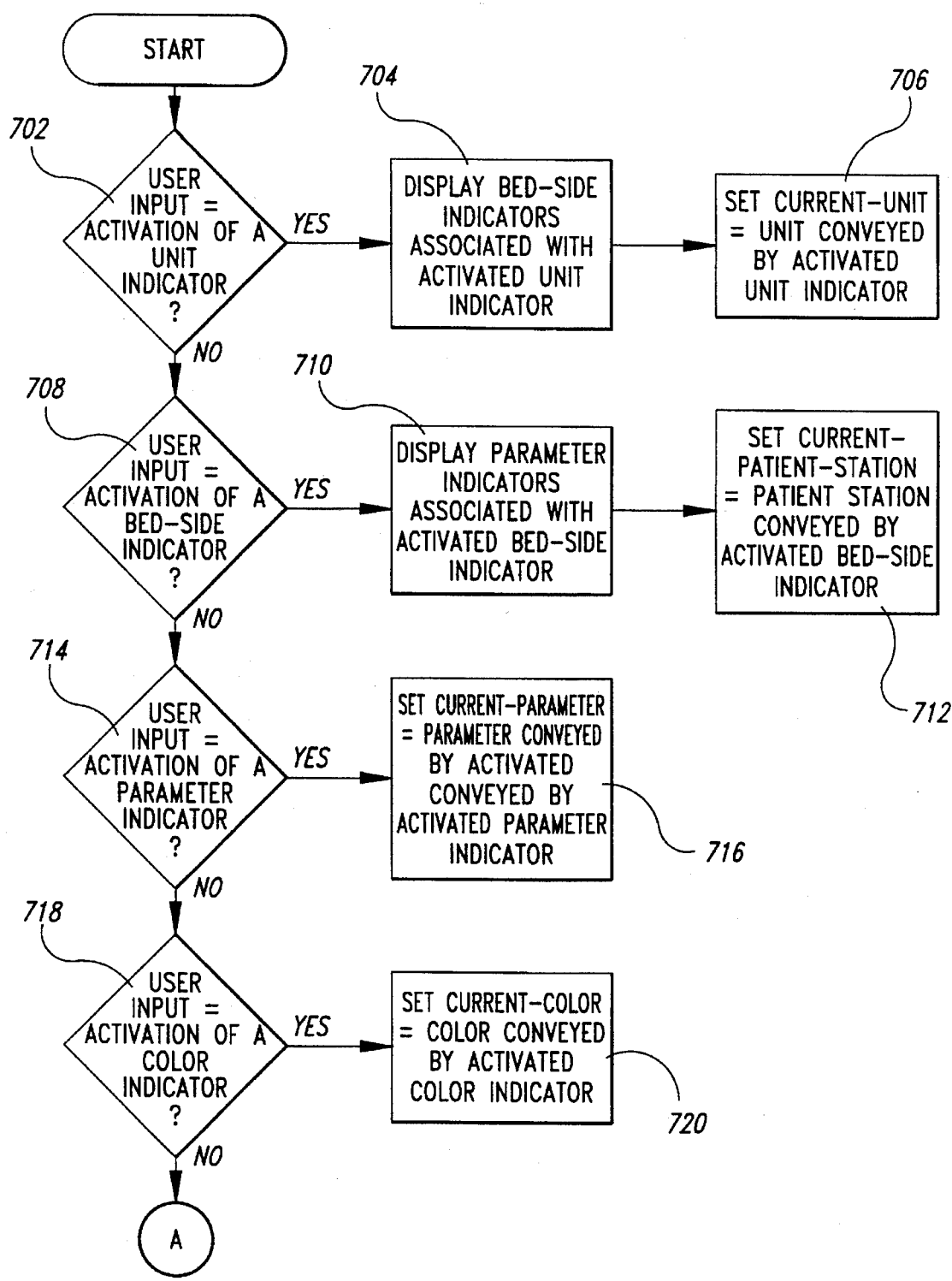
FIGS. 7A–7B comprise a flow diagram of a method for processing user input in accordance with a preferred embodiment of the present invention.
Figure 7B:
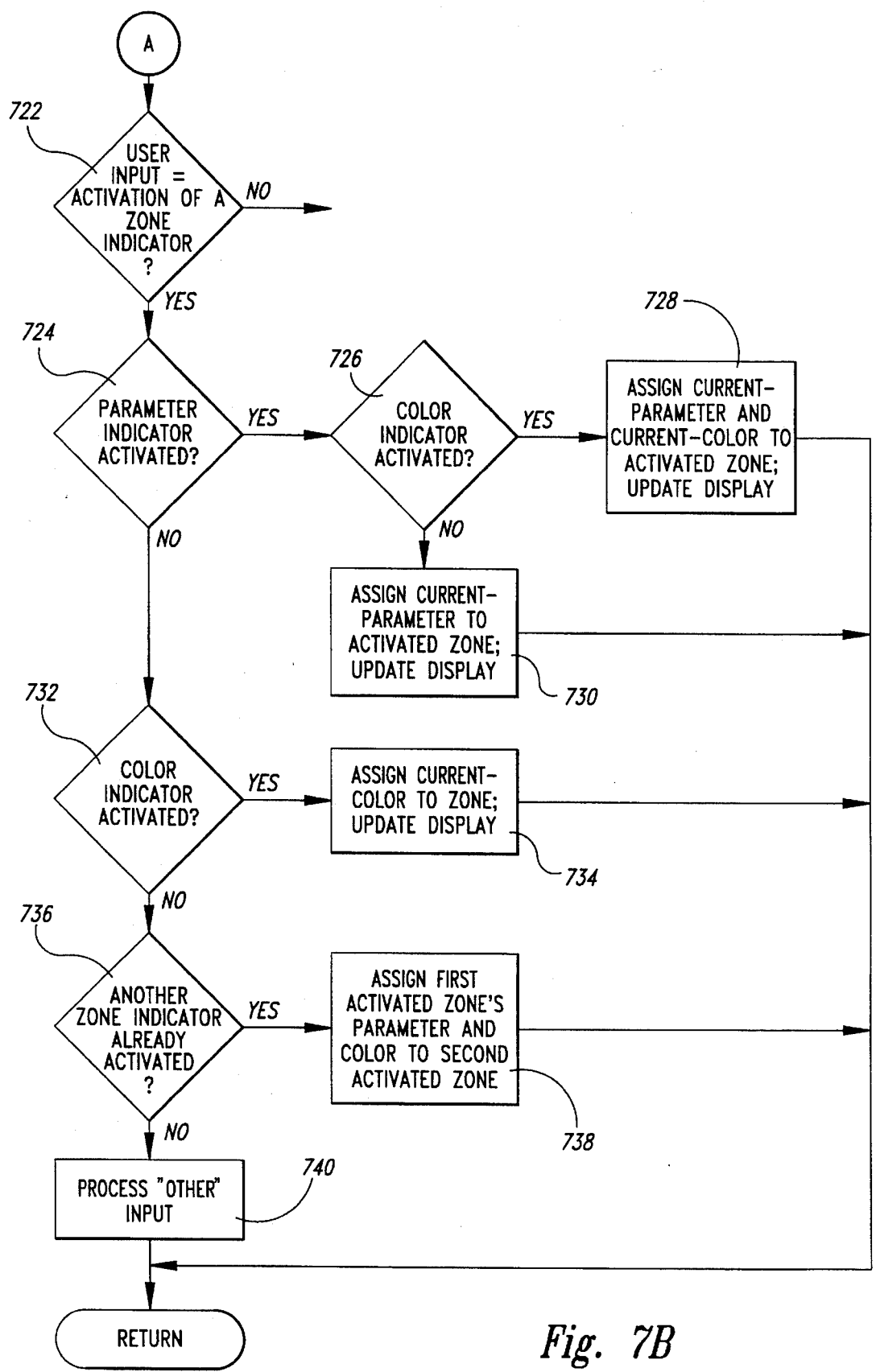

Referring back to FIG. 3, if the setup program determines in step 304 that the input was not from the monitoring network 100, i.e., system input, then in step 308 the setup program determines whether the input is from the graphical user interface 400, i.e. user input. If user input has occurred, then in step 310 the setup program processes the user input. FIGS. 7A–7B comprise a flow diagram of a method used by the setup program to process user input in accordance with a preferred embodiment of the present invention. In step 702, the setup program determines whether the user input is an activation of one of the unit indicators displayed on the video display. If the setup program determines that the user input is an activation of one of the unit indicators, then in step 704 the setup program displays the bed indicators associated with the activated unit indicator in the bed area. In step 706, the setup program sets a variable CURRENT-UNIT equal to the unit whose identity is conveyed by the activated unit indicator.

If the setup program determines in step 702 that the user input is not an activation of a unit indicator, then in step 708 the setup program determines whether the user input is an activation of one of the bed indicators displayed. If the user input is an activation of one of the bed indicators, then in step 710 the setup program displays the parameter indicators associated with the activated bed indicator. In step 712 the setup program sets a variable CURRENT-BED equal to the bed-side display station whose identity is conveyed by the activated bed indicator.

If the setup program determines in step 708 that the user input is not an activation of a bed indicator, then in step 714 the setup program determines whether the user input is an activation of one of the parameter indicators. If the user input is an activation of one of the parameter indicators, then in step 716 the setup program sets a variable CURRENT-PARAMETER equal to the parameter whose identity is conveyed by the activated parameter indicator. If the user input is not an activation of a parameter indicator, then in step 718 the setup program determines whether the user input is an activation of one of the color indicators. If the user input is an activation of one of the color indicators, then in step 720 the setup program sets a variable CURRENT-COLOR equal to the color whose identity is conveyed by the activated color indicator.

If the setup program determines that the user input is not an activation of one of the color indicators, then in step 722 of FIG. 7B, the setup program determines whether the user input is an activation of one of the zone indicators. If the user input is an activation of one of the zone indicators, then in step 724 the setup program determines whether one of the parameter indicators is activated. The setup program determines whether a parameter indicator is activated by determining what is stored in the variable CURRENT-PARAMETER. If a parameter indicator is activated, then in step 726 the setup program determines whether a color indicator is activated. The setup program determines whether a color indicator is activated by determining what is stored in the variable CURRENT-COLOR. If a color indicator is activated, then in step 728 the setup program assigns the value stored in the variable CURRENT-PARAMETER and the value stored in the variable CURRENT-COLOR to the display zone whose identity is conveyed by the activated zone indicator. The setup program also updates the display of the graphical user interface by displaying the activated parameter indicator in the color stored in CURRENT-COLOR and by displaying the activated zone indicator in the color stored in CURRENT-COLOR. Additionally, a textual label is displayed within the activated zone indicator to identify the parameter (and the bed-side transmitting the parameter) that will be displayed within the display zone whose identity is conveyed by the activated zone indicator.

If the setup program determines in step 726 that a color indicator is not activated, then in step 730 the setup program assigns the value stored in CURRENT-PARAMETER to the display zone whose identity is conveyed by the activated zone indicator. The setup program also updates the display of the graphical user interface by displaying a textual label within the activated zone indicator to identify the parameter (and the bed-side transmitting the parameter) that will be displayed within the display zone whose identity is conveyed by the activated zone indicator.

If the setup program determines in step 724 that a parameter indicator is not activated, then in step 732 the setup program determines whether a color indicator is activated. If a color indicator is activated but no parameter indicator is activated, then in step 734 the setup program assigns the value stored in the variable CURRENT-COLOR to the display zone whose identity is conveyed by the activated zone indicator. The setup program also updates the display of the graphical user interface by displaying the activated zone indicator in the color stored in CURRENT-COLOR. If a parameter assignment has previously been made to the activated zone indicator, then the parameter will be displayed in the color stored in CURRENT-COLOR.

If the setup program determines in step 732 that a color indicator is not activated, then in step 736 the setup program determines whether a second zone indicator is activated. If a user activates two consecutive zone indicators, then in step 738 the setup program assigns the first activated zone indicator's assigned parameter and color, if any, to the second activated zone indicator and clears the assignment for the first activated zone indicator. The setup program also updates the display of the graphical user interface to reflect the new assignments. If the setup program determines that the user input is not an activation of one of the indicators displayed on the video display device, then in step 740 the setup program processes the other input.

Returning to step 308 of FIG. 3, if the setup program determines that the input was not from the graphical user interface, i.e., user input, then in step 312 the setup program determines whether any bed-side monitor timers have expired. If the setup program determines that any bed-side monitor timers have expired, then in step 314 the setup program updates the display of the graphical user interface by removing the bed indicators corresponding to the bed-side monitors whose timers have expired. In step 316, the setup program determines whether the setup program has been terminated. If the setup program has been terminated, then in step 318 the setup program causes the graphical user interface 400 to be removed from the display screen 225 and the customized display of selected physiological parameters is then displayed. If the setup program has not been canceled, then steps 304–316 are repeated.

While various embodiments have been described in this application for illustrative purposes, the claims are not limited to the embodiments described herein. Equivalent devices or steps which operate according to principles of the present invention may be substituted for these described, and thus fall within the scope of the claims that follow.

I claim:

1. In a medical monitor having a display device, a method for controlling the display on the display device of a plurality of physiological parameters transmitted to the medical monitor by one or more medical sensors in response to the selection by a user of a parameter indicator, an attribute indicator, and a location indicator, the method comprising the steps of:

displaying on the display device each of a plurality of parameter indicators, each of the plurality of parameter indicators conveying the identity of one of the plurality of physiological parameters being transmitted to the medical monitor by the one or more medical sensors;

displaying on the display device each of a plurality of attribute indicators while displaying the plurality of parameter indicators, each of the plurality of attribute indicators conveying the identity of an attribute available for assignment to one of the plurality of physiological parameters, whereby the assignment of an attribute to a parameter causes the parameter to be displayed according to the assigned attribute on the display device;

displaying on the display device each of a plurality of zone indicators while displaying the plurality of parameter indicators and the plurality of attribute indicators, each of the plurality of zone indicators conveying the identity of a display zone on the display device available for assignment to one of the plurality of physiological parameters, whereby the assignment of a display zone to a parameter causes the parameter to be displayed within the assigned display zone on the display device:

receiving a signal indicating that the user has selected one of the displayed plurality of parameter indicators, one of the plurality of displayed attribute indicators, and one of the plurality of displayed zone indicators; and displaying on the display device the parameter whose identity is conveyed by the selected parameter indicator, according to the attribute whose identity is conveyed by the selected attribute indicator, within the display zone whose identity is conveyed by the selected zone indicator.

2. The method according to 1 wherein the medical monitor includes a pointing device and wherein the step of receiving a signal includes the step of receiving a signal originating in the pointing device indicating that the user has selected one of the displayed plurality of parameter indicators, one of the plurality of displayed color indicators, and one of the plurality of displayed zone indicators.

3. The method according to 1 wherein the medical monitor includes a keyboard device and wherein the step of receiving a signal includes the step of receiving a signal originating in the keyboard device indicating that the user has selected one of the displayed plurality of parameter indicators, one of the plurality of displayed color indicators, and one of the plurality of displayed zone indicators.

4. The method according to 1 wherein the step of receiving a signal includes the step of receiving a signal originating in a touch-sensitive video display device indicating that the user has selected one of the displayed plurality of parameter indicators, one of the plurality of displayed color indicators, and one of the plurality of displayed zone indicators.

5. The method according to 1 wherein the step of displaying a plurality of parameter indicators includes the step of receiving a signal from each of a plurality of medical sensors connected to the computer system.

6. The method according to claim 1 wherein the step of displaying each of a plurality of attribute indicators includes displaying each of a plurality of color indicators, each of the plurality of color indicators conveying the identity of a color available for assignment to one of the plurality of physiological parameters, whereby the assignment of a color to a parameter causes the parameter to be displayed in assigned color on the display device;

7. The method according to claim 1 wherein the step of displaying each of a plurality of attribute indicators includes displaying each of a plurality of tone indicators, each of the plurality of tone indicators conveying the identity of a tone available for assignment to one of the plurality of physiological parameters, whereby the assignment of a tone to a parameter causes the parameter to be generated in assigned tone;

8. In a computer implemented medical monitor, a method for controlling the display of physiological parameters in response to the activation of visual icons by a user, the physiological parameters being transmitted to the medical monitor by one or more medical sensors, the method comprising the steps of:

retrieving data representing a first and a second plurality of visual icons, each of the first plurality of visual icons visually conveying the identity of one of the physiological parameters available for display on the medical monitor, and each of the second plurality of visual icons visually conveying the identity of one of the display zones available for displaying a physiological parameter on the medical monitor;

simultaneously displaying on the medical monitor each of the first and second plurality of visual icons using the retrieved data representing the first and second plurality of visual icons;

receiving a signal indicating that the user has selected a parameter by activating one of the first plurality of displayed visual icons;

receiving a signal indicating that the user has selected a display zone by activating one of the second plurality of displayed visual icons; and transmitting an instruction to the medical monitor to display on the medical monitor the selected parameter in the selected display zone.

9. The method according to 8 further including the steps of:

retrieving data representing a third plurality of visual icons, each of the third plurality of visual icons visually conveying the identity of a color available for displaying a selected parameter on the medical monitor;

displaying each of a third plurality of visual icons using the retrieved data representing a third plurality of visual icons;

receiving a signal indicating that the user has activated one of the third plurality of displayed visual icons; and transmitting an instruction to the medical monitor to display the selected parameter in the selected color in the selected display zone.

10. The method according to 8 further including the steps of:

retrieving data representing a third plurality of visual icons, each of the third plurality of visual icons visually conveying the identity of a sound available for notifying the user of the existence of a condition associated with the selected parameter;

displaying each of a third plurality of visual icons using the retrieved data representing a third plurality of visual icons;

receiving a signal indicating that the user has activated one of the third plurality of displayed visual icons; and transmitting an instruction to the medical monitor to notify the user of the existence of the condition associated with the selected parameter using the selected sound.

11. In a patient monitoring network, a computer implemented medical monitor for displaying data comprising:

a unit area including a plurality of unit indicators displayed on the medical monitor, each of the plurality of unit indicators conveying the identity of a unit, one of the unit areas being selected responsive to user selection of a corresponding one of the plurality of unit indicators;

a bed area including a plurality of bed indicators displayed on the medical monitor, each of the plurality of bed indicators conveying the identity of a bed associated with a selected unit indicator, one of the bed areas being selected responsive to user selection of a corresponding one of the plurality of bed indicators;

a parameter area including a plurality of parameter indicators displayed on the medical monitor, each of the plurality of parameter indicators conveying the identity of only respective parameters associated with a selected bed indicator wherein parameters are displayed only for those parameters monitored at the selected bed area, one of the parameter areas being selected responsive to user selection of a corresponding one or more of the plurality of parameter indicators;

a color area including a plurality of color indicators displayed on the medical monitor, each of the plurality of color indicators conveying the identity of a color in which parameters identified by selected parameter indicators are displayed on the medical monitor, one of the color areas being selected responsive to user selection of a corresponding one of the color indicators for each selected parameter indicator;

a zone area including a plurality of zone indicators displayed on the medical monitor, each of the plurality of zone indicators conveying the identity of a display zone in which parameters identified by selected parameter indicators are displayed on the medical monitor, one of the display zone areas being selected responsive to user selection of a corresponding one of the zone indicators for each selected parameter indicator; and a memory for storing a program for receiving a signal indicating that the user has selected one of the displayed plurality of unit indicators and transmitting an instruction to display the bed indicators associated with the selected unit indicator, and for receiving a signal indicating that the user has selected one of the displayed bed indicators, one of the displayed color indicators, and one of the displayed zone indicators, and transmitting an instruction to display the parameter corresponding to the selected parameter indicator in the color corresponding to the selected color indicator on an area of the medical monitor corresponding to the selected zone indicators.

12. The medical monitor of claim 11 further including an input device connected to the medical monitor for transmitting to the memory the signal indicating that the user has selected one of the plurality of unit indicators, the signal indicating that the user has selected one of the plurality of bed indicators, the signal that the user has selected one or more of the plurality of parameter indicators, the signal that the user has selected one of the plurality of color indicators, and the user has selected one of the plurality of zone indicators.

13. The medical monitor of claim 11 in which the input device is a keyboard.

14. The medical monitor of claim 11 in which the input device is a pointing device.

15. The medical monitor of claim 11 in which the input device is a touch-sensitive video display device.

16. The medical monitor of claim 11, further including an input device connected to the medical monitor for transmitting to the medical monitor a signal indicating that the user has selected one or more of the plurality of parameter indicators, one of the plurality of color indicators for each selected parameter indicator, and one of the plurality of zone indicators for each selected parameter indicator.

17. The medical monitor of claim 16 wherein the memory further transmits an instruction to display the selected parameters for the selected bed with the selected color on the selected display zone of the medical monitor.

* * * * *